(12) United States Patent
Ferro et al.

(10) Patent No.: US 7,995,829 B2
(45) Date of Patent: Aug. 9, 2011

(54) METHOD AND APPARATUS FOR INSPECTING COMPONENTS

(75) Inventors: Andrew Frank Ferro, West Chester, OH (US); Patrick Joseph Howard, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 1042 days.

(21) Appl. No.: 11/832,442

(22) Filed: Aug. 1, 2007

(65) Prior Publication Data
US 2009/0034828 A1    Feb. 5, 2009

(51) Int. Cl.
*G06K 9/00* (2006.01)
*G21G 5/00* (2006.01)
*G01B 17/02* (2006.01)

(52) U.S. Cl. .................. 382/141; 382/149; 250/492.2; 73/627

(58) Field of Classification Search .................. 382/141, 382/132, 144, 149, 151, 152, 164, 171, 172, 382/173, 190, 201, 207, 254, 266, 283, 270, 382/199; 704/229; 73/602, 606, 627; 250/491.1, 250/492.2
See application file for complete search history.

(56) References Cited

U.S. PATENT DOCUMENTS

| | | | |
|---|---|---|---|
| 4,442,544 A | 4/1984 | Moreland et al. | |
| 4,468,704 A | 8/1984 | Stoffel et al. | |
| 4,501,016 A | 2/1985 | Persoon et al. | |
| 4,561,104 A | 12/1985 | Martin | |
| 4,751,846 A | 6/1988 | Dousse | |
| 4,809,349 A | 2/1989 | Herby et al. | |
| 4,823,194 A | 4/1989 | Mishima et al. | |
| 4,837,846 A | 6/1989 | Oyabu et al. | |
| 4,869,109 A | 9/1989 | Miglianico et al. | |
| 4,887,306 A | 12/1989 | Hwang et al. | |
| 4,908,875 A | 3/1990 | Assael et al. | |
| 5,047,851 A | 9/1991 | Sauerwein et al. | |
| 5,608,814 A | 3/1997 | Gilmore et al. | |
| 5,613,013 A * | 3/1997 | Schuette | 382/124 |
| 7,328,620 B2 * | 2/2008 | Howard et al. | 73/602 |
| 7,474,786 B2 * | 1/2009 | Naidu et al. | 382/168 |

* cited by examiner

*Primary Examiner* — Sheela Chawan
(74) *Attorney, Agent, or Firm* — William Scott Andes, Esq.; Armstrong Teasdale LLP

(57) ABSTRACT

A method for inspecting a component is provided. The method includes generating an image of the component, generating a signal indication mask, and generating a noise mask using a signal within the signal indication mask. The noise mask facilitates reducing a quantity of prospective signals contained in the signal indication mask. The method further includes utilizing the signal indication mask and the generated noise mask to calculate the signal-to-noise ratio of at least one potential flaw indication that may be present in the image.

20 Claims, 5 Drawing Sheets

METHOD AND APPARATUS FOR INSPECTING COMPONENTS

BACKGROUND OF THE INVENTION

This invention relates generally to the inspection of components and, more particularly, to a method and apparatus for performing nondestructive testing of fabricated components.

Where nondestructive evaluation of a workpiece or component is required, ultrasonic inspection techniques are used in many applications. One application of such ultrasonic inspection is in the inspection of gas turbine engine components such as rotors and blades, for example. Such components are typically formed from forging or casting a material with desired metallurgical properties. In the production of aerospace rotating components, the entire volume of the finished component is required to be inspected ultrasonically.

More specifically, there are many inspection or sensing applications where data are collected and stored for analysis. Certain types of applications are designed to detect signals from the ultrasonic probes or sensors in conditions where the background noise amplitude in the data varies greatly, for example, a variation of 6-12 dB, over the area of interest. In some applications signal features other than amplitude such as morphology or frequency can be used to help differentiate it from the background noise. However in some applications the only method to discriminate the signal from the background noise is relative amplitude or signal-to-noise ratio (SNR).

One example of such an application is the ultrasonic inspection of titanium forgings for material anomalies. This process creates two-dimensional or three-dimensional images with highly varying background noise caused by the underlying microstructures. However, the material anomalies for which the inspection is looking, e.g. hard-alpha, stress cracks, strain induced porosity, and foreign material, may have a morphology or frequency response which is similar to that produced by the microstructure. As a result, the inspector ultimately accepts or rejects the component being tested by detecting the presence of defect indications in these images in terms of their SNR.

For example, during the inspection process, the operator analyzes the ultrasound data to identify potential SNRs that may indicate a flaw. More specifically, the operator first locates a potential indication by manually searching each image for a suspect signal. Once the operator has identified a suspect signal, the operator manually draws a bounding box around the suspect signal. To complete the SNR calculation, the operator also determines a homogenous area of background noise surrounding the suspect signal. Statistics such as mean, max, and standard deviation are then applied to the data signal and noise areas to calculate the SNR for the indication. While this technique is acceptable for images having a homogenous background noise, this technique is less effective when the image includes variable background noise which obscures the homogenous noise thus making the selection of the signal by the operator both difficult and subject to operator interpretation.

BRIEF DESCRIPTION OF THE INVENTION

In one aspect, a method for inspecting a component is provided. The method includes generating an image of the component, generating a signal indication mask, and generating a noise mask using a signal within the signal indication mask. The noise mask facilitates reducing a quantity of prospective signals contained in the signal indication mask. The method further includes utilizing the signal indication mask and the generated noise mask to calculate the signal-to-noise ratio of at least one potential flaw indication that may be present in the image.

In another aspect, a signal detection system is provided. The signal detection system includes a probe and a processor coupled to the probe. The processor is programmed to generate an image of the component using the probe, generate a signal indication mask, and generate a noise mask based on the signal indication mask. The noise mask facilitates reducing a quantity of prospective signals contained in the signal indication mask. The processor is further programmed to calculate the signal-to-noise ratio of at least one potential flaw indication that may be present in the image using the signal indication mask and the generated noise mask.

DETAILED DESCRIPTION OF THE INVENTION

As used herein, the term "component" may include any component that may be imaged such that an image with variable noise and/or a variable background structure is generated. For example, in one embodiment, a component is any signal of interest that may be imaged. Another example of a component is a component that is configured to be coupled within a gas turbine engine and that may be coated with a wear-resistant coating, for example a turbine shroud support. A turbine shroud support is intended as exemplary only, and thus is not intended to limit in any way the definition and/or meaning of the term "component". Furthermore, although the invention is described herein in association with a gas turbine engine, and more specifically in association with a rotor for a gas turbine engine, it should be understood that the present invention is applicable to other turbine engine stationary components and rotatable components, power system components, pipe line components, and/or any other component that may be imaged such that an image with variable noise and/or a variable background structure is generated. Accordingly, practice of the present invention is not limited to rotors for a gas turbine engine, but rather, the present invention may be used to find and classify signals in any image that may include variable noise and/or a variable background structure.

Furthermore, although the invention is described herein in association with an ultrasonic testing apparatus, it should be understood that the present invention is applicable to other nondestructive testing methods and/or techniques, such as, for example, Eddy-Current testing, infrared and/or thermal testing, X-ray testing, magnetic resonance testing, and/or any other nondestructive testing methods and/or techniques that generate an image with variable noise and/or a variable background structure. The present invention is also applicable to other signal detection methods and/or techniques, such as, for example, medical imaging, astronomical imaging, satellite imaging, and/or any other signal detection methods and/or techniques that generate an image with variable noise and/or a variable background structure. Accordingly, practice of the present invention is not limited to ultrasonic testing, but may be used to find and classify signals in any image that may include variable noise and/or a variable background structure. As such, the term "probe" as used herein, may include any device that may be used to acquire signal data.

Figure 1:
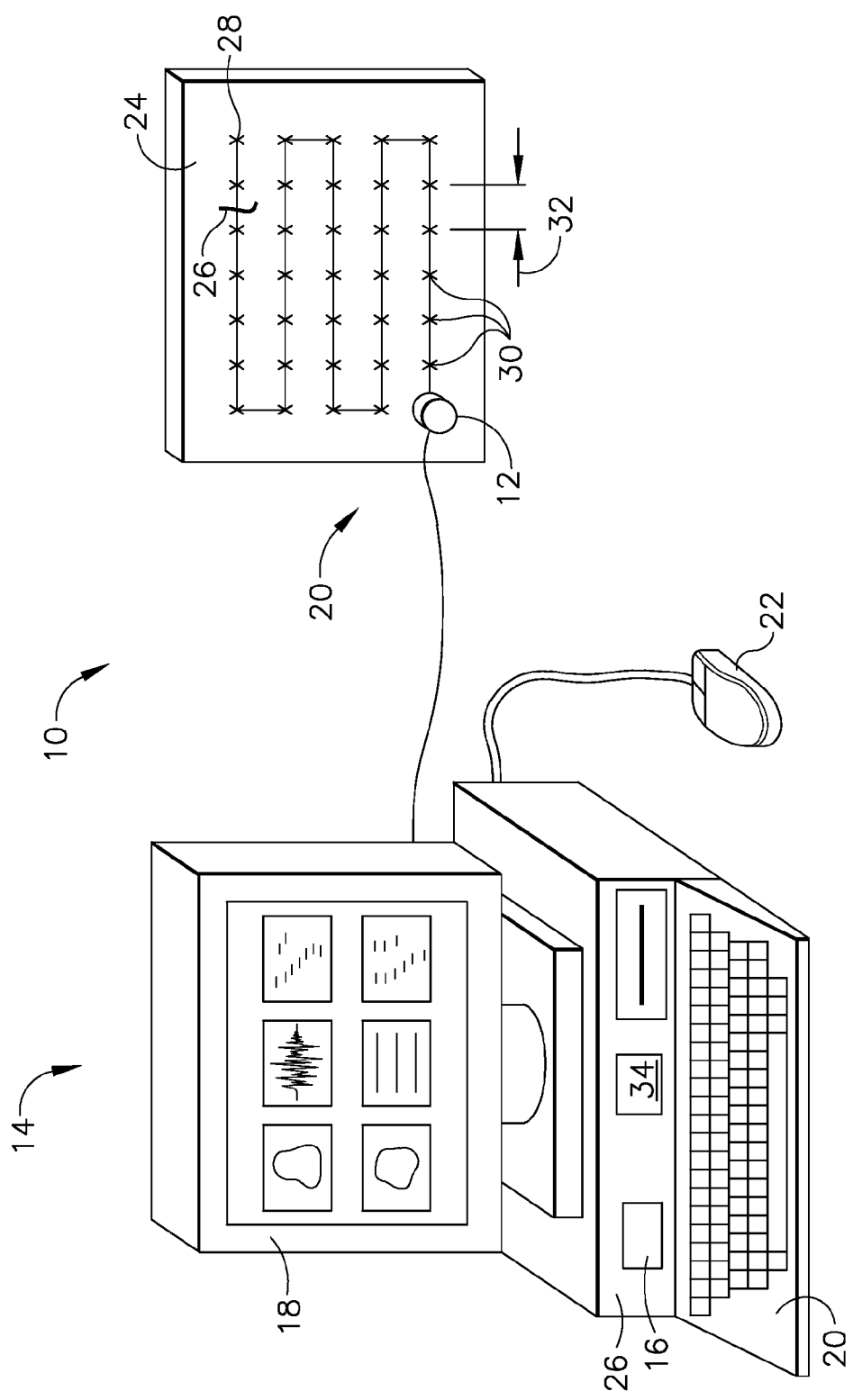
FIG. 1 is a schematic view of an exemplary embodiment of an ultrasound system.

FIG. 1 is a schematic view of an exemplary embodiment of an ultrasound system 10 that includes a probe or a pulse echo transducer 12 coupled to a control unit 14 including a processor 16, a display 18, a keyboard 20 and a mouse 22. As used herein, the term "processor" is not limited to just those integrated circuits referred to in the art as processors, but broadly refers to computers, processors, microcontrollers, microcomputers, programmable logic controllers, application specific integrated circuits, and other programmable circuits. Control unit 14 is configured to acquire, analyze and display ultrasonic test data. In the exemplary embodiment, ultrasound system 10 is a pulse echo (PE) ultrasound test apparatus that uses a single transducer located on one side of the component that functions as both a transmitter and a receiver. Using pulse echo testing only requires access to one side of the test component. In various embodiments ultrasound system 10 may include an electromechanical apparatus for moving transducer 12 across the surface of the test component and the electromechanical scanning apparatus may include one or more position sensors that monitor the position of the moving transducer.

In use, transducer 12 is placed in acoustical conduct with a component 24 to be tested and ultrasound is introduced to component 24. In one embodiment, a known acoustic gel is placed between component 24 and transducer 12 to facilitate sound transfer between component 24 and transducer 12. In another embodiment, component 24 and transducer 12 are placed proximate each other submerged in a liquid that facilitates ultrasound wave travel through the liquid. In an exemplary embodiment using the liquid in an automated setting, system 10 includes a rotatable table (not shown) including at least one collet or mandrel (not shown). Component 24 is automatically chucked in the collet or onto the mandrel and the table is rotated or translated such that component 24 remains in close proximity to transducer 12 during a scan. Transducer 12 emits ultrasonic energy which is at least partially reflected when an interface 26 is encountered within component 24 (such as a discontinuity, inclusion or microcrack) or at an interface on a far side (relative to transducer 12) of component 24 between component 24 and the liquid. When the ultrasound wave contacts the interface, a portion of the sound energy is reflected back through the component toward ultrasonic transducer 12. Ultrasonic transducer 12 may be used as both a transmitter that produces RF sound wave pulses and as a receiver that records the reflected RF sound wave signals. The time between when an RF pulse is transmitted and an RF reflection is received equals the time it took for the sound wave to pass into the test component, contact the area of discontinuity, and travel back to the ultrasonic transducer 12. Thus, the time between transmission and reception is related to the depth of the discontinuity. The amplitude of the RF signal is related to the magnitude of the discontinuity, as the more reflective the discontinuity, the more sound energy is reflected back towards the ultrasonic transducer 12.

In one embodiment, ultrasonic transducer 12 is located on a mechanical arm (not shown) whose movement is precisely controlled by control unit 14. The mechanical arm moves the ultrasonic transducer 12 over the surface of test component 24 in a precisely controlled scan during testing. The mechanical arm moves the ultrasonic transducer 12 from a starting point 28. As ultrasonic transducer 12 moves across test component 24, ultrasonic test data is taken at preprogrammed data points 30. In the exemplary embodiment, data points 30 are equally spaced apart a distance 32. In an alternative embodiment, control unit 14 is programmed to take data at irregular distances. Position sensors (not shown) may be used to facilitate determining a position of ultrasonic transducer 12 during a scan. The position data may then be used to reconstruct test component 24 in ultrasound images.

As ultrasonic transducer 12 receives the reflected sound waves at an individual data point 30, the information is passed to control unit 14 in the form of an RF signal. This RF signal is digitized by control unit 14 and the resulting digitized data is passed to and stored as a data array in a memory 34 within control unit 14. The location on test component 24 from which each set of digitized data originated can be determined by knowing the scan pattern and by knowing the position of the digitized data in the data array.

Figure 2:
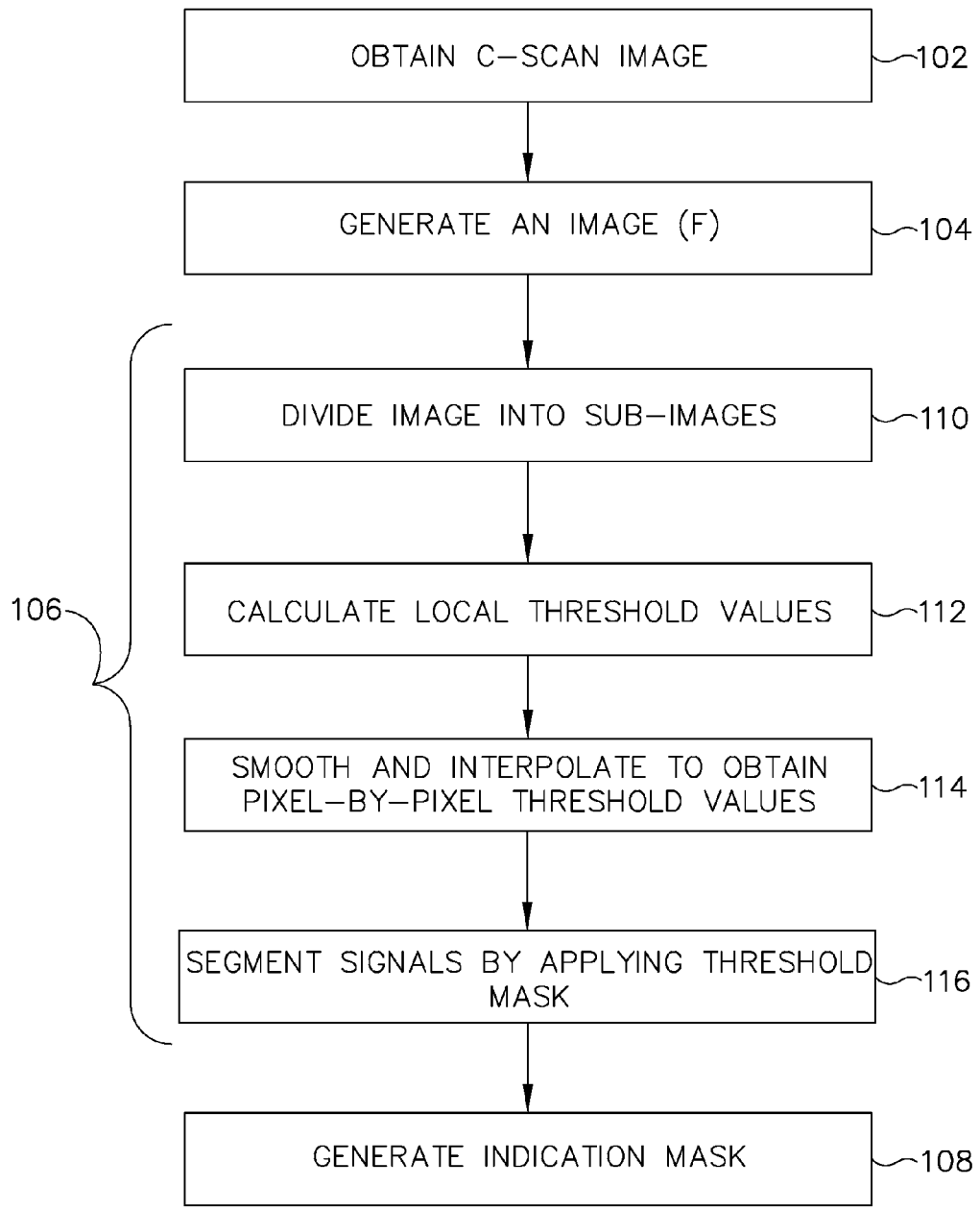
FIG. 2 is a flow chart illustrating an exemplary method 100 for detecting potential flaws in an ultrasound C-scan image.

FIG. 2 is a flow chart illustrating an exemplary method 100 for detecting flaws in an ultrasound C-scan image. Method 100 includes obtaining 102 a C-Scan image, generating 104 an ultrasound image F of an object, such as, for example, component 24 (shown in FIG. 1), and generating 106 an indication mask 108 of the ultrasound image F. In the exemplary embodiment, generating an indication mask 108 includes dividing 110 image F in sub-images, calculating 112 local threshold values, smoothing and interpolating 114 to obtain pixel-by-pixel threshold values, and segmenting 116 signals by applying a threshold mask.

As discussed above, during the scanning process, the ultrasound system 10 scans the component 24 with sound along a surface thereof. At each location (x,y) on the component 24 the ultrasonic transducer 12 is pulsed by system 10 to send a sound wave through the component 24 which reflects off or echoes back signals from the part to the transducer 12. The maximum amplitude values of the reflected signals are then digitized and stored in a data processor 16, thereby defining a C-scan image F of the component 24 which is suitable for image viewing via display 18.

The method further includes an automatic defect recognition step 106 that is utilized to generate the indication mask 108. More specifically, in C-scanning, pixel data values f(i,j) are obtained for each pixel (i,j) of the C-scan image F, thus defining a $M_1 \times M_2$ pixel image. The data processor 16 includes image processing software which enables the pixel data values f(i,j) to be converted to binary flaw-no flaw values b(i,j) as will be described in detail below.

Once the pixel data values f(i,j) are obtained for the $M_1 \times M_2$ C-scan image F, a dividing step 110 is performed which logically divides the image F into K subimages or regions of dimension $N_1 \times N_2$, denoted $G_k$, wherein k=1, ... K. In the exemplary embodiment, subregion includes pixel data values g(i,j). For example, if a 2048×1024 pixel image F is used, the image may be broken down into 128 subimages each having 128×128 pixels therein. It should be realized that the above subimage size is exemplary only, and may vary based on the overall pixel size of the image F. The size and shape of the subimages is a design parameter which can be selectively chosen relative to the size of the image F to achieve a desired level of performance. Generally, the smaller the subimage, the smaller the indication which can be identified by the method of the present invention.

Preferably, the first subimage $G_1$ is defined in a corner of the image, and the remaining subimages $G_k$ for k=2, ..., K, are selected using a raster scanning convention, thereby defining the subimages in a manner which preserves the spatial correlation of the image.

Once the subimages are defined, a local threshold is calculated at step 112 to calculate a threshold level y(k) for each of the subimages $G_k$. In one embodiment, the local threshold may be calculated in accordance with the following equations:

$$y(k)=y(k-1)+A_3(k) \quad (1)$$

$$A_3=h_3(A_2(k)) \quad (2)$$

$$A_2(k)=A_1(k)-y(k-1) \quad (3)$$

$$A_1(k)=h_1(G_k) \quad (4)$$

wherein, $A_1(k)$ is a first adjusted value which is calculated from the pixel data values g(i,j) in each subimage $G_k$ using the function denoted $h_1$ as shown in equation (4). Preferably, the first adjusted value is the mean plus some multiple of the standard deviation of the pixel data values g(i,j) in each subimage, but depending on the particular application, the maximum, minimum, mean, median, or other suitable first adjusted value may be used. The choice of the first adjusted value is a design parameter which can be selectively chosen based on the type of metal used or indications one desires to identify.

Figure 3:
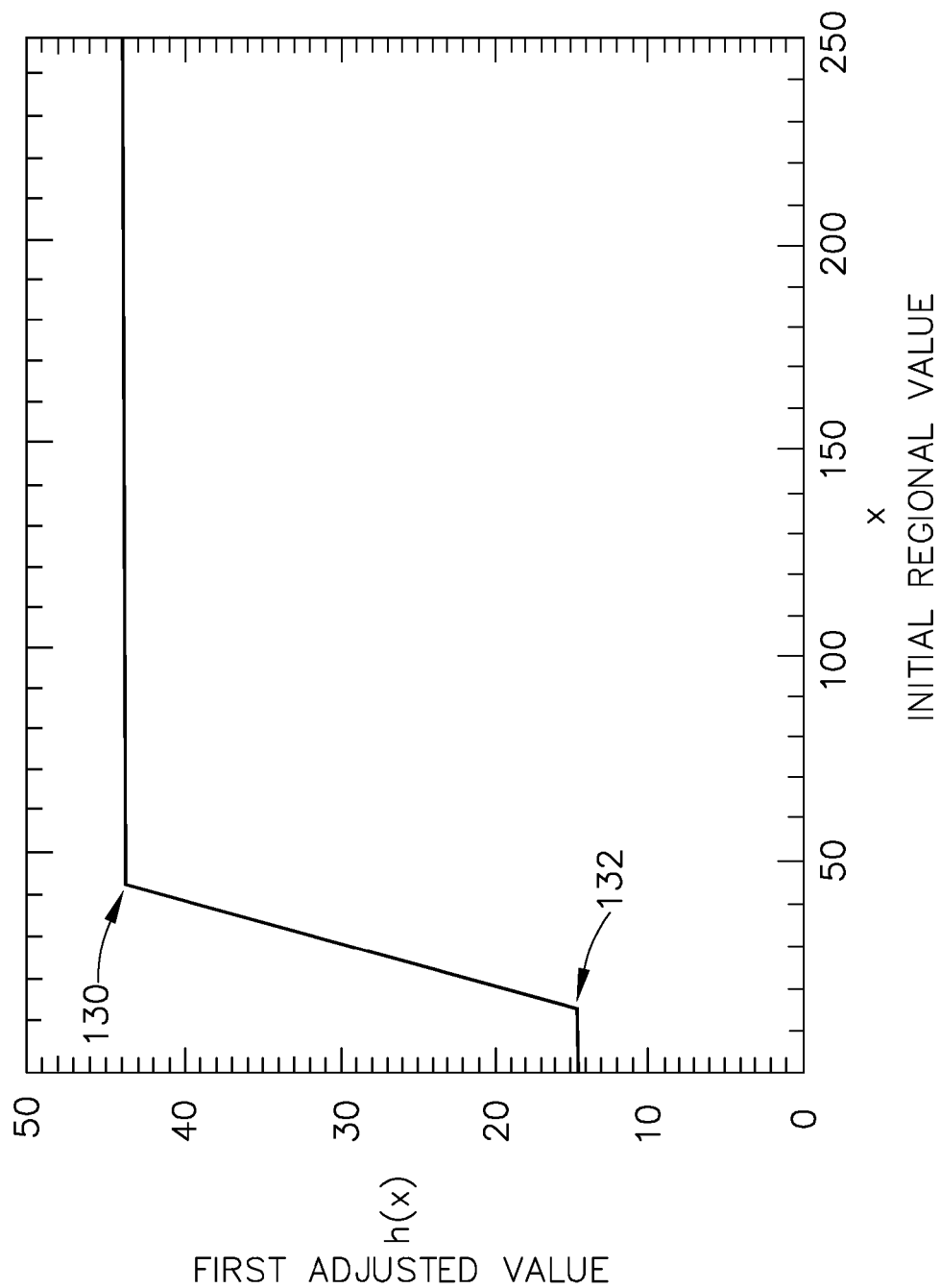
FIG. 3 is a graphical illustration of an adjustment function that may be utilized with the method shown in FIG. 2.

A second adjusted value, $A_2(k)$ may then be calculated by subtracting from the first adjusted value $A_1(k)$ the preceding regional threshold level, y(k−1) as shown in equation (3). A third adjusted value, $A_3(k)$ can be calculated from the second adjusted value $A_2(k)$ using the function $h_3$ which is selectively chosen to match the particular characteristics of the data acquisition system used in C-scanning the component to obtain the pixel data values f(i,j). A preferred embodiment of the function $h_3$ is shown in FIG. 3, which is particularly suited for use with data values collected from an 8-bit C-scan data acquisition system. As shown in FIG. 3, the function $h_3$ is preferably a non-linear function which includes upper and lower saturation points 130 and 132, respectively, and is linear between the saturation points. The saturation points 130 and 132 operate to provide upper and lower limits for the third adjusted values of each subimage.

While the function $h_3$ of FIG. 3 represents a preferred embodiment of the adjustment function $h_3$, the saturation points 130 and 132 and/or the shape of the function $h_3$ may be different depending on the particular characteristics of the system in which the method is used. For example, the functional $h_3$ may be determined based on the type or dynamic range of the data acquisition system used, the amount of attenuation or gain which is applied to the ultrasonic signals, the length of the gate in the metal, and/or the size or type of indication to be identified. In other words, the particular adjustment function $h_3$ is a design parameter which can be selectively defined based on the particular inspection procedure and/or requirements of the application in which the present invention is used.

In addition to incorporating information about the data acquisition process, function $h_3$ is a weighting function which acts similar to a forgetting factor in an adaptive filter. The function $h_3$ determines the "memory" of the procedure by defining how to weight the information from the present subimage $G_k$ (contained in the second adjusted value, $A_2(k)$ relative to information from the previous subimage $G_k-1$ (contained in y(k−1)) in calculating the threshold level y(k) for the present subimage $G_k$. Preferably, the function $h_3$ is a constant function such as $h_3(X)=0.5(X)$ in the linear range, but any other suitable weighting function may be used. Thus, function $h_3$ is a design parameter which can selectively be defined to adjust the performance of the present method.

As can be seen from equation (1), the regional threshold level y(k) for each subimage $G_k$ is determined by adding the third adjusted value, $A_3(k)$ to the previous regional threshold level y(k−1) for subimage $G_{k-1}$. Maintaining consistency between the defining and numbering of the subimages and the spatial correlation of the object, as discussed above, enables the present method to take advantage of the previous threshold level when calculating the next threshold level. Thus, equations (1)-(4) function as a moving weighted average in calculating the threshold levels for each region.

In order to enable initialization of the threshold procedure of equation (1), a threshold level y(1) must be defined for subimage $G_1$. This can be achieved by using the value of the adjustment function $h_1$ corresponding to an initial regional value calculated from data values g(i,j) in subregion $G_1$, or by any other suitable means which enables initialization of the procedure.

Once the regional threshold levels y(k) are determined for each subimage $G_k$, the neighborhood averages of the regional threshold levels y(k) are utilized to generate a new set of regional threshold levels z(k) using a neighborhood $L_k$ in accordance with:

$$z(k) = \frac{1}{l_1 - l_2} \sum_{y(j) \in L_k} y(j) \quad (5)$$

where $y(j) \in L_k$ is each of the y(j)'s included in $L_k$. The neighborhood averaging is performed to take into account the fact that the raster scanning convention used to define the subimages is causal, and noise correlation in C-scan images is typically non-causal. Since the procedure of equation (1) only takes into account information from subimages which are prior in time to the present subimage in calculating the regional threshold value of the present subimage, the neighborhood averaging enables the method to take into account all of the information near or around the present subimage, regardless of whether it is prior in time or not. For example, the neighborhood $L_k$ may be defined such that the regional threshold level y(k) of subimage $G_k$ is averaged with all of the regional threshold levels of subimages which are directly adjacent to subimage $G_k$, thereby determining a new regional threshold level z(k) for subimage $G_k$.

While the step of neighborhood averaging is preferably used in the present method, it is an optional step which, when used, can provide a higher probability of flaw detection and/or a less probability of false flaw indication in some applications. However, it has been found that neighborhood averaging may have only a small or negligible effect on flaw identification in some applications. Thus, in certain applications the neighborhood averaging step can be eliminated to simplify the present method.

Once the regional threshold levels y(k) or z(k) are determined, an interpolation step 114 is performed in which pixel threshold values t(i,j) are computed for each pixel (i,j) of the image F from the regional threshold values using interpolation. The interpolation step is performed to ensure continuity between subimage boundaries by smoothing the threshold levels out between the regions, thereby eliminating the occurrence of large differences in the threshold levels between adjacent pixels at the boundaries of subimages. Preferably, linear interpolation is used to determine the pixel threshold levels t(i,j).

Once pixel threshold levels t(i,j) are determined, the signals are segmented 116 to generate an indication mask 108. Specifically, binary values b(i,j) are determined to generate the indication mask 108 based on a comparison between the pixel data values f(i,j) and the pixel threshold values t(i,j). The indication mask 108 preferably includes $M_1 \times M_2$ binary data values which make up the indication mask 108. For example, the binary values b(i,j) may be determined as follows:

$$b(i, j) = \begin{bmatrix} 1, f(i, j) \geq t(i, j) \\ 0, \text{otherwise} \end{bmatrix} \quad (6)$$

Thus, a binary value of 1 would identify an indication such as a flaw or a large grain in the metal at the corresponding location thereon, and a binary value of 0 would indicate that no flaw in the metal exists at that particular location.

In the exemplary embodiment, the particular criteria for selecting the binary values in equation (6) may vary depending on the particular application. For example, in some applications a binary value of 1 may be selected if the data value f(i,j) is greater than, rather than greater than or equal to the pixel threshold values t(i,j). Conversely, in some data acquisition systems in which the present method could be employed, it may be desirable to identify an indication if the pixel data value f(i,j) is below, rather than above the corresponding pixel threshold value t(i,j).

Figure 4:
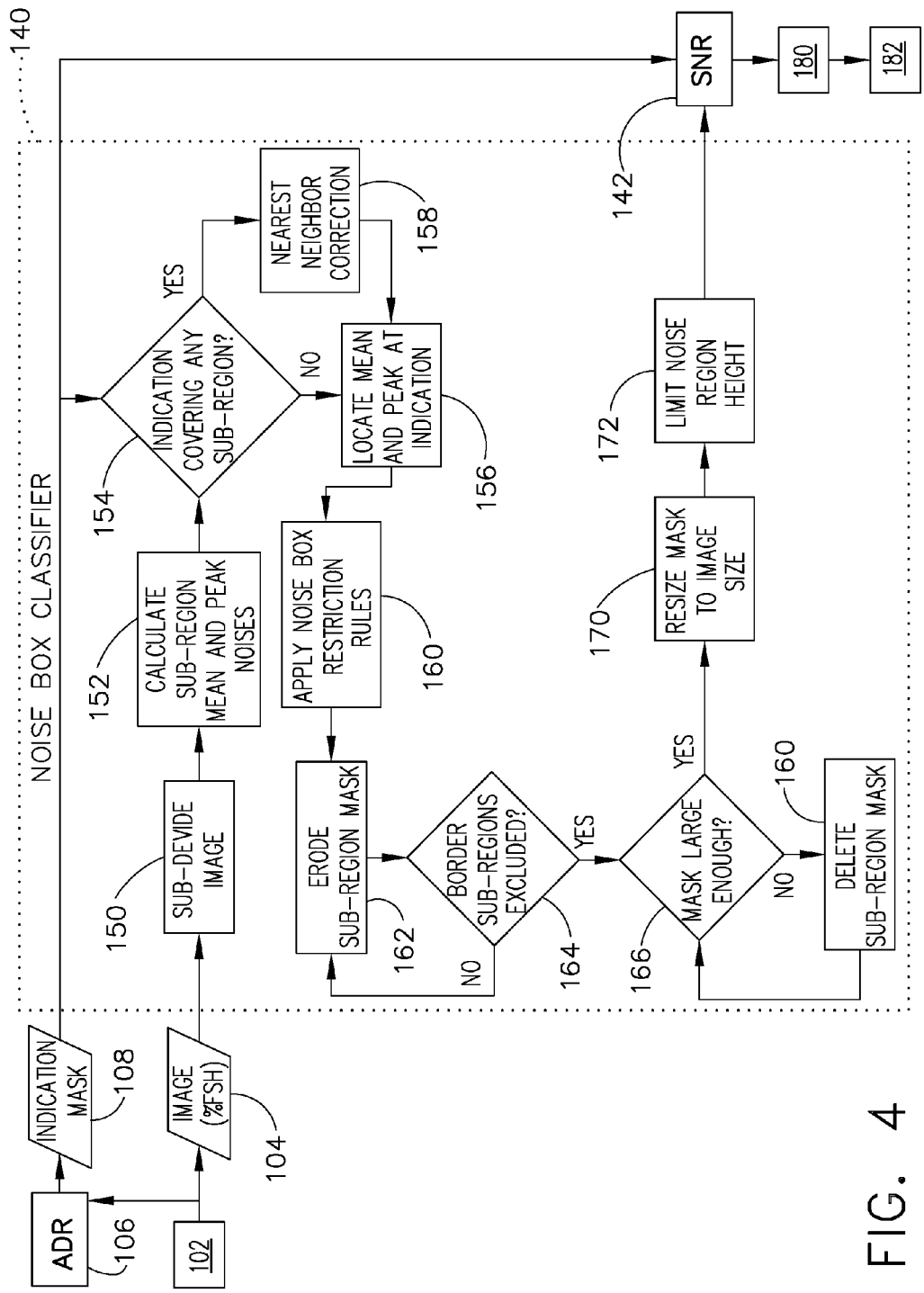
FIG. 4 is a flow chart illustrating an exemplary method of classifying potential flaws detected using the method illustrated in FIG. 2.

FIG. 4 shows a flow chart illustrating an exemplary method of classifying potential flaws detected using the method illustrated in FIG. 2. In the exemplary embodiment, once the indication mask 108 has been generated as described above, the indication mask 108 is transmitted to both the noise box classifier 140 to facilitate generating a noise mask and a signal-to-noise ratio (SNR) calculation algorithm 142. In the exemplary embodiment, noise box classifier 140 is a program or algorithm that is installed on a processor, such as, for example, processor 16 (shown in FIG. 1).

In the exemplary embodiment, noise box classifier 140 is programmed to automatically locate or identify a homogenous noise area within image F (generated at step 104 shown in FIG. 2) and to generate a mask that includes this homogenous noise region. The homogenous noise mask is then transmitted to the SNR calculation algorithm 142. The SNR calculation algorithm 142 is then programmed to calculate the SNR of any signals that are located in the indication mask 108 (generated using the method shown in FIG. 2).

Referring to FIG. 4, at step 150, image F is logically divided into C subimages or regions of dimension $D_1 \times D_2$, denoted $R_c$, wherein c=1, . . . , C. In the exemplary embodiment, a subimage includes pixel data values r(i,j). For example, if an image having 2048×1024, is used, the image may be broken down into subimages containing 5×30 pixels, i.e. 150 pixels, and therefore contain a total of 14,350 subimages therein. It should be realized that the above subimage size is exemplary only, and may vary based on the overall pixel size of the image F. The size and shape of the subimages is a design parameter which can be selectively chosen relative to the size of the image F to achieve a desired level of performance or may be chosen based on the class of images to be examined. Generally, the smaller the subimage, the more spatially adaptive the noise mask will be by the method of the present invention.

Once the subimages are defined, a local mean value and a local peak value are determined 152 for each prospective signal in the subimage $R_c$. Specifically, assuming each exemplary subimage $R_c$ includes 150 pixels as described above, the mean value is calculated by determining the pixel intensity value for each pixel in the subimage $R_c$, and dividing the sum of the pixel intensity values by the total quantity of pixels in the subimage $R_c$. Additionally, at step 152, the peak pixel intensity value is determined. That is, the pixel within the subimage having the highest intensity value is identified. The mean pixel intensity value and the peak pixel intensity value will be discussed further below. As a result, an array is identified that includes a mean value and a peak value for each subimage operated on by the noise box classifier 140.

At step 154, noise box classifier 140 determines if a signal identified in the signal indication mask 108 is covering a subregion defined in step 150. More specifically, noise box classifier 140 is programmed to identify any signal indications within the signal indication mask 108 that substantially cover the subimage $R_c$. For example, assuming that step 154 determines that approximately 80% of the subimage $R_c$ is covered, i.e. 80% of the data within the subimage is potentially invalid, or not part of the noise region, then the method proceeds to step 158. However, if at step 154, noise box classifier 140 determines that less than 80% of the subimage $R_c$ is covered, then the data within the subimage $R_c$ is presumed to be valid and the noise box classifier proceeds to step 156. It should be noted that the coverage area of 80% as used herein is exemplary only, and the coverage area may be modified to any suitable percentage.

As discussed above, if at step 154 noise box classifier 140 determines that a predetermined percentage of the subimage $R_c$ is covered, then the mean and peak noise values or statistics generated in step 152 are not utilized to locate a mean and peak indication as will be discussed below. Rather, noise box classifier 140 is programmed at step 158 to perform a nearest neighbor correction on the subimage. During operation, the nearest neighbor correction or algorithm determines the corrected intensity vector for the pixel and transmits this corrected intensity to step 156. Optionally, if noise box classifier 140 determines that a predetermined percentage of the subimage $R_c$ is not covered, then the mean and peak noise values or statistics generated in step 152 could be utilized to locate mean and peak noise value seeds for the indication at step 156.

At step 156, the mean and peak values generated in step 152, or, alternatively, a different local neighborhood of pixels, are utilized to locate the mean and peak noise value seeds for the indication signals within image F. As a result, step 156 generates two numbers, the mean noise pixel value seed for each indication in image F and the peak noise pixel value seed for each indication in image F. More specifically, as discussed above, at step 152 a mean value and a peak value is generated for each subimage $R_c$ in image F. At step 156, a mean value and a peak value for noise region seeding is determined for each indication in the indication mask 108 by utilizing the mean and peak values determined in step 152, or those calculated from a compatible nearby region to each indication in question.

At step 160, noise box restriction rules are applied to connected components region growing using the mean pixel values and the peak pixel values determined in step 156. More specifically, in this step, the values calculated in step 156 are "grown" by a predetermined range, measured in decibels. For example, assuming the mean value determined in step 156 is thirty counts, growing the region by /−6 decibels with the mean restriction rules in step 160 will grow the region comprised of mean subimage values to between fifteen and sixty counts. That is, the noise box region growing restriction rules describe the bounds on the connected grown region, for both the mean and peak subregion values determined in step 152.

The preferred method for growing by connectivity is the unity distance criterion, which does not consider diagonally neighboring elements to be connected. The grown regions for these criteria are then combined with a logical intersection to form an initial grown noise region mask.

At step 162 the grown region is eroded utilizing the values determined in step 160. More specifically, each subregion image is dynamically eroded to facilitate excluding bordering noise regions that may be present adjacent to the grown region. After the erosion algorithm has eroded the grown noise region a first time, the eroded mask is sent to step 164 wherein it is determined whether the border regions have been excluded. If the border regions have not been excluded, the algorithm returns to step 162 wherein the image is further eroded with a refined structuring element used from the previous iteration. However, if at step 164 it is determined that the border regions have been eroded, the algorithm proceeds to step 166.

At step 166 it is determined whether the noise mask is too small to permit further image processing. For example, if at steps 162 and 164 the subimage is reduced to a quantity of pixels that is too few to permit a valid noise region, the mask is dilated or grown in step 166 to ensure that a predetermined quantity of pixels are present in the noise region for validity. In the exemplary embodiment, the predetermined quantity of pixels is preset based on the class of images being processed. Optionally, if at step 166 it is determined that the subimage includes the minimum quantity of pixels to permit further processing, the method proceeds to step 170.

At step 170, the noise mask is resized such that the noise mask is, for example, exactly the same size as the original image 108. At step 172, the noise region height in the noise mask generated at step 170 is limited. More specifically, the noise mask height of the signals within the noise mask is limited to a predetermined height in number of pixels.

Referring again to step 142, the noise mask generated by the noise box classifier 140 and the signal indication mask 108 (generated using the method shown in FIG. 2) are utilized to calculate the signal-to-noise ratio (SNR) of the potential flaw signals. More specifically, the mask values (1 or 0) for each pixel in the signal indication mask 108 are multiplied by the pixel value of each corresponding pixel in the original image F and a signal statistic is generated with the remaining "signal" pixels. Similarly, the mask values (1 or 0) for each pixel in the noise mask generated by noise box classifier 140 are multiplied by the pixel value of each corresponding pixel in the original image F and noise statistics are generated with the remaining "noise" pixels. The signal and noise statistics are then mathematically combined to calculate the SNR.

The SNR output parameter calculated from step 142 is then used to classify 180 the potential indications originally detected by the indication mask generation step 106. That is, the field of SNRs calculated for each indication defines the classification space for determining whether the indication should be called out or not. Depending on the class of images under evaluation, the SNR classification is a threshold per indication found that will either continue to classify the found signal as an indication, or pass the signal as a non-rejectable feature of the component's image. In the exemplary embodiment, the results of the SNR algorithm 142 may be output 182 to, for example, but not limited to, display 18, a printer (not shown), a data storage device (not shown), such as, a hard drive, a CD-ROM, a floppy disk, and/or a USB storage device, and/or any other suitable output location. The output of the SNR algorithm 142 may include, but is not limited to including, the signals classified as an indication.

Figure 5:
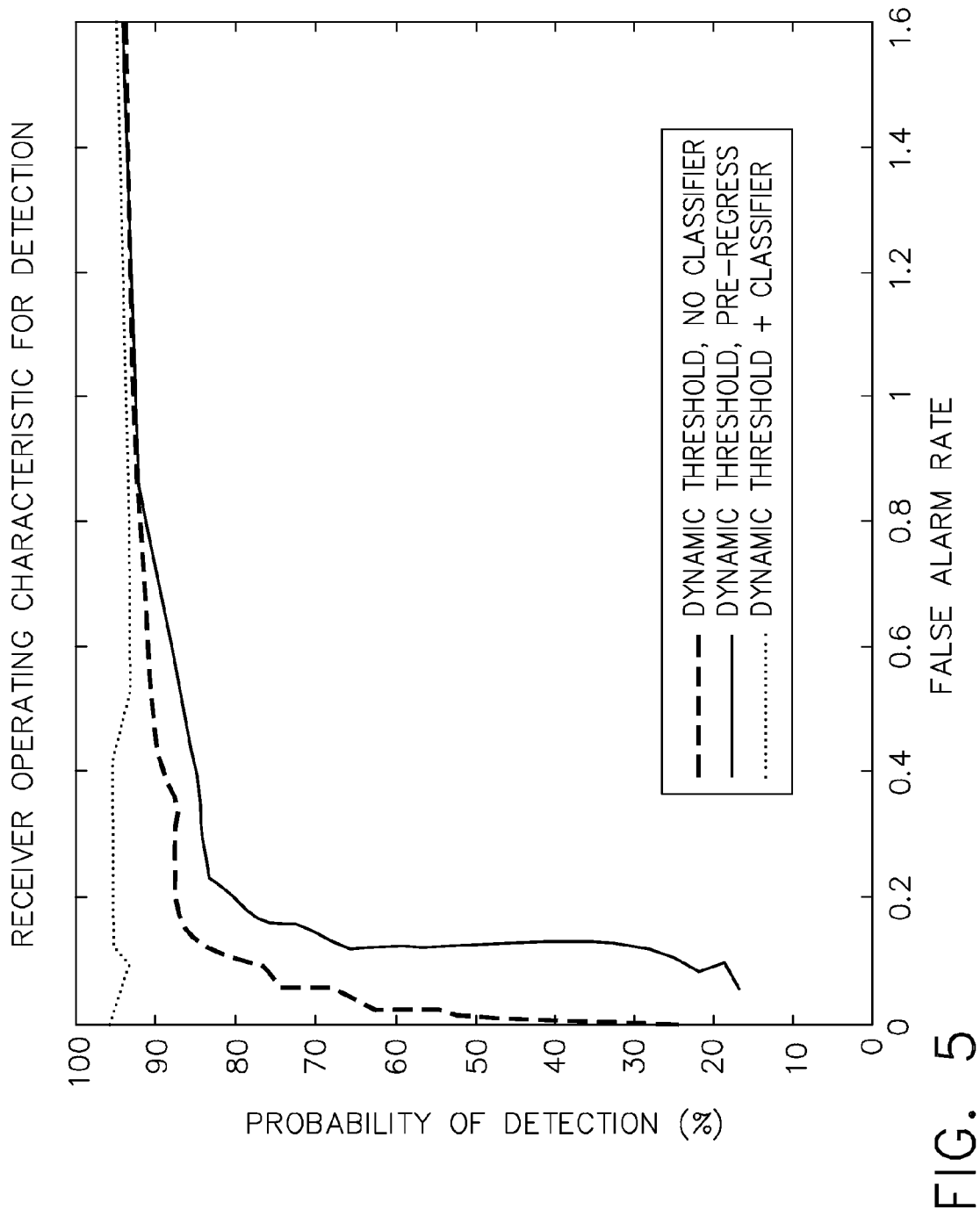
FIG. 5 is a graphical illustration of an exemplary relationship between a probability of signal detection and a false call rate using the methods illustrated in FIGS. 2 and/or 4.

FIG. 5 is a graphical illustration of the algorithm operating under different optimizing conditions, showing the relationship between a probability of signal detection and false call rate. By varying the SNR threshold, the operating point for the algorithm can be chosen easily, depending on the optimal point on the curve. By changing the parameter set of the algorithm, different characteristic curves may also been generated.

Described herein is an ultrasound inspection system that is programmed to detect flaw signals in an ultrasound image having a variable noise pattern based on amplitude in a manner that is easily adjusted for different image classes. More specifically, the method utilizes a dynamic threshold and an SNR-based classifier. During operation, the dynamic threshold identifies prospective flaw signals by using the algorithm illustrated in FIG. 2. This algorithm may be tuned to segment prospective flaw signals from the background noise over a wide range of image classes.

The output of the dynamic threshold is then fed into the SNR-based classifier. The classifier reduces the set of prospective signals utilizing an automated SNR calculation that is based on a local area of homogeneous noise. The output from the SNR-based classifier is a set of relevant signals within the image, that substantially eliminate any false positives that may be produced by the dynamic threshold portion of the algorithm. In addition, the classifier may be adjusted for a wide variety of image classes by adjusting the SNR value. For example, in one class of images, material anomalies of interest may have an SNR of 4.0 or greater. In this case the classifier may be set to return only signals that meet that criterion. For a second class of images, however, material anomalies of interest may have an SNR of 2.5 or greater. In this case, the automatic signal recognition software may be modified to change the value of the SNR in the classifier from 4.0 to 2.5. As such, the automatic signal recognition software described herein is applicable to a wide class of images without involving an image processing expert.

During operation, by optimizing the algorithm described in FIG. 2, the probability of signal detection was improved by greater than 95% by utilizing the classifier shown in FIG. 4. The classifier is programmed to accurately calculate the SNR of any detected signal by applying a combination of region growing and morphology. Specifically, while maintaining a set of heuristics, an irregularly shaped noise region is traced around the signal. The noise region includes only the homogenous noise defined by the localized statistics found nearby to the signal. The algorithm then filters any of the prospective indications whose SNRs were decidedly below the threshold criteria resulting in a decrease in the false positive rate on the validation set to approximately 0%, thereby increasing the accuracy of the SNR calculations.

Accordingly, FIG. 2 illustrates an exemplary signal detection algorithm that stresses the adjustable nature of the algorithm. The algorithms described herein provide a standard to enable inspectors to agree on the results, given the common noise region established by the indication classification process. The algorithm further generates accurate SNR measurements, thus effectively reducing inspection cycle time and complexity and providing precise detection reproducibility. In the exemplary embodiment, the SNR measurements may be used to automatically make a disposition of the component being tested and/or signal being detected. For example, the SNR measurements may indicate the presence of a material anomaly, such as, but not limited to, a crack, hard-alpha, porosity, foreign material, and/or any other microstructure characteristics that may be used for making a disposition of a tested component. As such, the above-described methods and apparatus facilitate automatically making a determination of whether a component includes an anomaly in its material structure.

A technical effect of the various embodiments of the systems and methods described herein include at least one of improving the detection of near surface discontinuities in objects being scanned. The above-described methods and apparatus are cost-effective and highly reliable for improving near surface resolution of an ultrasound inspection system. The methods and apparatus describe collecting ultrasound waveform data for an inspection area and surface echoes over a two-dimensional grid of points on the component being inspected. The waveform data from the area around the surface signals are post-processed using signal and image processing techniques. The result is an improved near surface resolution. The resulting data can then be further processed for the detection of signals of interest in the inspection either by an automated detection algorithm or by manual review. The methods and apparatus described above facilitate fabrication, assembly, and reducing the maintenance cycle time of components in a cost-effective and reliable manner.

Exemplary embodiments of methods and apparatus for automatically making a disposition for a component are described above in detail. The method and apparatus are not limited to the specific embodiments described herein, but rather, components of the method and apparatus may be utilized independently and separately from other components described herein. For example, the methods may also be used in combination with other nondestructive testing and/or other signal detection methods and/or techniques, and is not limited to practice with only the ultrasound system as described herein. Rather, the present invention can be implemented and utilized in connection with many other nondestructive testing and/or signal detection applications.

While the invention has been described in terms of various specific embodiments, those skilled in the art will recognize that the invention can be practiced with modification within the spirit and scope of the claims.

What is claimed is:

1. A method for inspecting a component, said method comprising:
   generating an image of the component reflected RF sound wave signals;
   generating a signal indication mask of the image by:
      dividing the image into sub-images;
      calculating a local threshold value for each of the sub-images;
      smoothing and interpolating to obtain pixel by pixel threshold values that substantially eliminates the occurrence of large differences the threshold levels between adjacent pixels at the boundaries of the sub-images; and
      segmenting the signals by applying a threshold mask and based on a comparison between the pixel data values and the pixel-by-pixel threshold values;
   generating a noise mask using a signal within the signal indication mask, wherein the noise mask facilitates reducing a quantity of prospective signals contained in the signal indication mask; and
   utilizing the signal indication mask and the generated noise mask to calculate the signal-to-noise ratio of at least one potential flaw indication that may be present in the image.

2. A method in accordance with claim 1 further comprising classifying the at least one potential flaw based on the corresponding calculated signal-to-noise ratio.

3. A method in accordance with claim 1 wherein generating a noise mask further comprises dividing the generated image into a plurality of subimages.

4. A method in accordance with claim 1 wherein generating a noise mask further comprises calculating at least a mean pixel value and a peak pixel value for each of a plurality of subimages.

5. A method in accordance with claim 1 wherein generating a noise mask further comprises comparing each of a plurality of subimages of the generated image with a corresponding one of a plurality of subimages of the generated signal indication mask.

6. A method in accordance with claim 1 wherein generating a noise mask further comprises locating at least a mean noise pixel value seed and a peak noise pixel value seed in at least one of a plurality of subimages of the generated image.

7. A method in accordance with claim 6 wherein generating a noise mask further comprises applying a pre-determined rule set to each of the plurality of subimages, wherein the pre-determined rule set is based on at least the mean noise pixel value seed and the peak noise pixel value seed.

8. A method in accordance with claim 1 wherein generating a noise mask further comprises eroding a boundary of a subimage of the generated image.

9. A method in accordance with claim 1 wherein utilizing the signal indication mask and the noise mask to calculate the signal-to-noise ratio of at least one potential flaw indication further comprises combining the signal indication mask and the noise mask.

10. A method in accordance with claim 1 wherein utilizing the signal indication mask and the noise mask to calculate the signal-to-noise ratio further comprises:
    combining values of the signal indication mask with values of the generated image; and
    combining values of the noise mask with the values of the generated image.

11. A signal detection system comprising:
    a probe; and
    a processor coupled to said probe, said processor programmed to:
    generate an image of the component using said probe;
    generate a signal indication mask;
    generate a noise mask based on the signal indication mask wherein the noise mask includes an identified a homonous noise area within the image, and, wherein the noise mask facilitates reducing a quantity of prospective signals contained in the signal indication mask; and
    calculate the signal-to-noise ratio of at least one potential flaw indication that may be present in the image using the signal indication mask and the generated noise mask.

12. A signal detection system in accordance with claim 11 wherein said processor is further programmed to classify the at least one potential flaw based on the corresponding calculated signal-to-noise ratio.

13. A signal detection system in accordance with claim 11 wherein said processor is further programmed to divide the generated image into a plurality of subimages.

14. A signal detection system in accordance with claim 11 wherein said processor is further programmed to calculate at least a mean pixel value and a peak pixel value for each of a plurality of subimages.

15. A signal detection system in accordance with claim 11 wherein said processor is further programmed to compare each of a plurality of subimages of the generated image with the generated image.

16. A signal detection system in accordance with claim 11 wherein said processor is further programmed to locate at least a mean noise pixel value seed and a peak noise pixel value seed in at least one of a plurality of subimages of the generated image.

17. A signal detection system in accordance with claim 16 wherein said processor is further programmed to apply a pre-determined rule set to each of the plurality of subimages, wherein the pre-determined rule set is based on at least the mean noise pixel value seed and the peak noise pixel value seed.

18. A signal detection system in accordance with claim 11 wherein said processor is further programmed to erode a boundary of the generated noise mask.

19. A signal detection system in accordance with claim 11 wherein said processor is further programmed to combine the generated signal indication mask and the generated noise mask.

20. A signal detection system in accordance with claim 11 wherein said processor is further programmed to:
  combine values of the signal indication mask with values of the generated image; and
  combine values of the noise mask with the values of the generated image.

* * * * *